United States Patent [19]

Gu

[11] Patent Number: 5,731,348

[45] Date of Patent: Mar. 24, 1998

[54] ALKYLCARBOXY AMINO ACIDS-MODULATORS OF THE KAINATE RECEPTOR

[75] Inventor: Zi-Qiang Gu, Rosemont, Pa.

[73] Assignee: Bearsden Bio, Inc., Philadelphia, Pa.

[21] Appl. No.: 600,330

[22] Filed: Feb. 13, 1996

Related U.S. Application Data

[63] Continuation-in-part of Ser. No. 389,916, Feb. 15, 1995, abandoned.

[51] Int. Cl.$^6$ ............................................. A61K 31/195
[52] U.S. Cl. ............................................................. 514/561
[58] Field of Search ............................................. 514/561

[56] References Cited

U.S. PATENT DOCUMENTS

| | | | |
|---|---|---|---|
| 3,412,147 | 11/1968 | Kollonitsch et al. | 260/534 |
| 4,889,855 | 12/1989 | Jacobsen et al. | 514/250 |
| 4,904,681 | 2/1990 | Cordi et al. | 514/380 |
| 5,061,721 | 10/1991 | Cordi et al. | 514/376 |
| 5,086,702 | 2/1992 | Trullas et al. | 514/531 |
| 5,364,876 | 11/1994 | Hamilton | 514/381 |

FOREIGN PATENT DOCUMENTS

| | | |
|---|---|---|
| WO 94/27602 | 12/1994 | WIPO . |
| WO 96/25387 | 8/1996 | WIPO . |

OTHER PUBLICATIONS

Alekseeva, L., et al., "Synthesis and Study of Fluorine–containing Metabolite Analogs," Chemical Abstracts 75(5):565 (Aug. 2, 1971) Abstract No. 36618.

Bergmann, and Chun–Hsu, "Organic Fluorine Compounds: Pard XLVI[1], 7–Fluoroglutamic Acid and Fluorofolic Acid," Synthesis 44–46 (1973).

Dorville, A., et al, "Preferred Antagonist Binding State of the NMD Receptor: Synthesis, Pharmacology, and Computer Modeling of (Phosphonomethyl)phenylalanine Derivative [1,2]," J. Med. Chem. 35:2551–2562 (1992).

Hansen, J., et al., "Structural Conformational and Steriochemical Requirement sof Central Excitatory Amino Acid Receptors," Med. Res. Rev. 10(1):55–94 (1990).

Ishida, M., et al., "Changes in Preference for Receptor Subtypes of configurational Variants of a Glutamate Analog: Conversion from the NMDA–type to the Non–NMDA Type," Brain Research, 550:152–156 (1991).

Ohfune and Shimamoto, "Design, Synthesis and Excitatory Activity of Conformationally Restricted L–Glutamate Analogues in the Mammalian Central Nervous System," Trends Med. Chem. '90, Proc. Int. Symp. Med. Chem., 11th 175–182 (1992).

Wong, L., et al., "Willardiines Differentiate Agonist Binding Sites for Kainate–Versus AMPA–preferring Glutamate Receptors in DRG and Hippocampal Neurons," Chemical Abstracts 121(3):189 (Jul. 18, 1994) Abstract No. 27615.

Ault and Hildebrand, "Activation Of Nociceptive Reflexes By Peripheral Kainate Receptors", J. Pharmacology And Experimental Therapeutics, 265(2):927–932 (1992).

Ault and Hildebrand, "Effects of Excitatory Amino Acid Receptor Antagonists On A Capsaicin–evoked Nociceptive Reflex: A Comparison With Morphine, Clonidine And Baclofen", Pain, 52:341–349 (1993).

Benita, et al., "Characterization Of Drug–Loaded Poly(d, l–lactide) Microspheres", J. Pharm. Sci., 73:1721–1724 (1984).

Buehler and Pearson, "Survey of Organic Synthesis", Wiley–Interscience Publication, New York, (1970), pp. v–vii.

Coderre, "The Role Of Excitatory Amino Acid Receptors And Intracellular Messengers in Persistent Nociception After Tissue Injury In Rats", Molecular Neurobiology, 7:229–246 (1993).

Dray, et al., "Pharmacology Of Chronic Pain", TIPS, 15:190–197 (1994).

Greensein and Winitz, (editors), "Chemistry Of Amino Acids" Kreiger Publishing, Malabar, Florida, 3:2438–2445 (1984).

Gu, et al., "Synthesis, Resolution, And Biological Evaluation Of The Four Stereoisomers Of 4–Methylgutamic Acid: Selective Probes Of Kainate Receptors", J. Med. Chemistry, 38(14):2518–2520 (1995).

Gu and Hesson, "A Highly Diastereoselective Synthesis Of 4–Alkyl Threo Glutamic Acids", Tetrahedron: Asymmetry, 6(9):2101–2104 (1995).

Gu, et al., "Diastereoselective Synthesis Of (2S, 4R)–4–Methylglutamic Acid (SYM 2081): A High Affinity And Selective Ligand At The Kainate Subtype Of Glutamate Receptors", Bio. & Med. Chem. Ltr., 5(17):1973–1976 (1995).

Huettner, "Glutamate Receptor Channels In Rat DRG Neurons: Activation By Kainate And Quisqualate And Blockade Of Desensitization By Con A", Neuron, 5:255–266 (1990).

Hutchinson, et al., "4–(Phosphonoalkyl)–And 4–(Phosphonoalkenyl)–2–piperidinecarboxylic Acids: Synthesis, Activity At N–Methyl–D–aspartic Acid Receptors, And Anticonvulsant Acitivity", J. Med. Chem., 32:2171–2178 (1989).

Lehmann, et al., "7–Chlorokynurenate Prevents NMDA–induced And Kainate–induced Striatal Lesions", Brain Res., 620:1–6 (1993).

(List continued on next page.)

Primary Examiner—William R. A. Jarvis
Attorney, Agent, or Firm—Arnall, Golden & Gregory, LLP

[57] ABSTRACT

Compounds of a new class of alkyl carboxy amino acid analogs of glutamic acid act as specific regulators of the kainic acid EAA receptor cation channel. These compounds are useful for treating neurological, neuropsychological, neuropsychiatric, neurodegenerative, neuropsychopharmacological and functional disorders associated with excessive or insufficient activation of the kainic acid subtype of the ionotropic EAA receptors; treating cognitive disorders associated with deactivation, suboptimal activation or overactivation of the kainic acid receptor; alleviating pain and improving and enhancing memory, learning, and associated mental processes. A method for designing novel AMPA or kainic acid receptor agonists or antagonists is also disclosed.

6 Claims, 3 Drawing Sheets

OTHER PUBLICATIONS

London, et al., "Specific Binding Of [$^3$H]kainic Acid To Receptor Sites In Rat Brain" *Molecular Pharmacology*, 15:492–5–5 (1979).

Mao, et al., "Differential Roles Of NMDA And Non–NMDA Receptor Activation In Induction And Maintenance Of Thermal Hyperalgesia In Rats With Painful Peripheral Mononeuropathy", *Brain Res.*, 598:271–278 (1992).

Mathiowitz and Langer, "Polyanhydride Microspheres As Drug Carriers I. Hot–Melt Microencapsulation", *J. Controlled Release*, 5:13–22 (1987).

Mathiowitz, et al., "Novel Microcapsules For Delivery Systems", *Reactive Polymers*, 6:275–283 (1987).

Mathiowitz, et al., "Polyanhydride Microspheres As Drug Carriers. II. Microencapsulation By Solvent Removal", *J. Appl. Polymer Sci.*, 35:755–774 (1988).

Mathiowitz, et al., "Morphology Of Microsphere Delivery Systems", *Scanning Microscopy*, 4:329–340 (1990).

Mathiowitz, et al., "Polyanhydride Microspheres, IV. Morphology And Characterization Of Systems Made By Spray Drying", *J. Appl. Polymer Sci.*, 45:125–134 (1992).

Murphy, et al., "Binding Of [$^3$H]–3–(2–carboxypiperazin–4–yl–D–propyl–1–phosphonic acid) To Rat Membranes: A Selective, High Affinity Ligand Of N–methyl–D–aspartate Receptors" *J. Pharm. Exper. Therapeutics*, 240:778–784 (1987).

Murphy, et al., "Characterization Of Quisqualate Recognition Sites In Rat Brain Tissue Using [$^3$]alpha–amino–3–hydroxy–5–methylisoxazole–4–propionic Acid And A Filtration Assay", *Neurochemical Research*, 12:775–781 (1987).

H. J. Overman, et al., "Structure\Activity Relations Of N–Methyl–D–Aspartate Receptor Ligands As Studied By Their Inhibition Of [$^3$H]D–2–Amino–5–Phosphonopentanoic Acid Binding In Rat Brain Membranes", *Neuroscience*, 26(1):17–31 (1988).

Rappé, "UFF, A Full Periodic Table Force Field For Molecular Mechanics And Molecular Dynamics Simulations", *J. Amer. Chem. Soc.*, 114:10,024 (1992).

Remington's Pharmaceutical Sciences 17th Edition, Chapter 76:1418 (1985).

Tal and Bennett, "Neuropathic Pain Sensations Are Differentially Sensitive To Dextrophan", *Neuro. Report*, 5:1438–1440 (1994).

Trullas, et al., "Functional Antagonists At The NMDA Receptor Complex Exhibit Antidepressant Actions", *Eur. J. Pharm.*, 185:1–10 (1990).

Woo and Jones, "Asymmetric Synthesis From α–Amino Acids: Some Reactions Of (S)–Pyroglutamate", *Tet. Lett.* 32(47):6949–6952 (1991).

Pharmacophore Model

ALKYLCARBOXY AMINO ACIDS-MODULATORS OF THE KAINATE RECEPTOR

This application is a continuation-in-part of U.S. Ser. No. 08/389,916, filed Feb. 15, 1995, now abandoned, the disclosure of which is incorporated herein by reference.

BACKGROUND OF THE INVENTION

This invention generally relates to the Kainic acid (KA) subtype of the postsynaptic glutamate receptor and more specifically to compounds other than KA which bind to the KA receptor and methods of use thereof, and to a method of designing new compounds which modulate the glutamate receptors.

During the past twenty years a revolution in understanding the basic structure and chemistry of the synaptic interconnections of neural tissues has taken place which has yielded knowledge relevant to the treatment of neural tissue damage and disorders. The studies have centered around an understanding of the properties of the neurochemical transmitters released from presynaptic membranes and, most importantly, the postsynaptic receptors for these transmitters. The nicotinic acetylcholine and γ-aminobutyric acid (GABA) receptors have been characterized and found to be under the control of allosteric modulators. During the past ten years a great deal of attention has been directed to the excitatory amino acids (EAAs), principally glutamic acid (the primary excitatory neurotransmitter) and aspartic acid, and their receptors since these amino acids mediate the fast excitatory transmission in the mammalian central nervous system. Thus, glutamic acid can bring about changes in the postsynaptic neuron that reflect the strength of the incoming neural signals.

Two major classes of EAA receptors are distinguished: ionotropic and metabotropic. The ionotropic receptors contain ligand-gated ion channels and mediate ion fluxes for signaling, while the metabotropic receptors use G-proteins for signaling. Further sub-classification of the ionotropic EAA glutamate receptors is based upon the agonists (stimulating agents) other than glutamic and aspartic acid that selectively activate the receptors. Presently, it is believed that there are three major subtypes of ionotropic glutamate receptors based on binding at defined concentrations: 1) a receptor responsive to N-methyl-D-aspartate (NMDA); 2) a receptor not responsive to NMDA but responsive to α-amino-3-hydroxy-5-methyl-4-isoxazolepropionic acid (AMPA); and 3) a receptor not responsive to NMDA but responsive to KA. The NMDA receptor controls the flow of both divalent ($Ca^{++}$) and monovalent ($Na^+$, $K^+$) ions into the postsynaptic neural cell although it is the $Ca^{++}$ flux which is of the greatest interest. The AMPA and KA receptors also regulate the flow into postsynaptic cells of monovalent $K^+$ and $Na^+$ and occasionally divalent $Ca^{++}$.

EAA receptors have been implicated during development in specifying neuronal architecture and synaptic connectivity, and may be involved in experience-dependent synaptic modifications. These receptors have also drawn interest since they appear to be involved in a broad spectrum of CNS disorders. For example, during brain ischemia caused by stroke or traumatic injury, excessive amounts of the EAA glutamic acid are released from damaged or oxygen deprived neurons. Binding of this excess glutamic acid to the postsynaptic glutamate receptors opens their ligand-gated ion channels, thereby allowing an ion influx which in turn activates a biochemical cascade resulting in protein, nucleic acid and lipid degradation and cell death. This phenomenon, known as excitotoxicity, is also thought to be responsible for the neurological damage associated with other disorders ranging from hypoglycemia, ischemia, and epilepsy to chronic neurodegeneration in Huntington's, Parkinson's, and Alzheimer's diseases.

Drugs acting on the ionotropic EAA receptors are, therefore, expected to have enormous therapeutic potential. U.S. Pat. No. 4,904,681 to Cordi, et al., teaches the use of a compound, D-cycloserine, which modulates the NMDA receptor to improve/enhance memory and to treat cognitive deficits linked to a neurological disorder. U.S. Pat. No. 5,061,721 to Cordi et al. teaches the use of a combination of D-cycloserine and D-alanine to treat Alzheimer's disease, age-associated memory impairment, learning deficits, and psychotic disorders, as well as to improve memory or learning in healthy individuals. U.S. Pat. No. 5,086,072 to Trullas et al. discloses the use of another compound, 1-aminocyclo-propane carboxylic acid (ACPC), which modulates the NMDA receptor, to treat mood disorders including major depression, bipolar disorder, dysthymia and seasonal affective disorder. Trullas et al., also teaches that ACPC mimics the actions of clinically effective antidepressants in animal models, and that ACPC and its derivatives may be used to treat neuropharmacological disorders resulting from excessive activation of the NMDA receptor.

The EAA receptors are also involved with the physiological basis for drug addiction. In U.S. Ser. No. 08/121,100, Maccecchini has demonstrated that not only tolerance to, but also dependence on, opiates can be prevented by a partial agonist of the NMDA receptor. Presently, it is believed that a balance in the activities of the three types of EAA ionotropic receptors may be necessary to achieve normal neurological synaptic control. It is known that, in the presence of excess glutamic acid, antagonists of the NMDA receptor prevent immediate excitotoxicity. However, over a longer period of time, all cell death is not completely prevented, which may be due to the excitotoxicity caused by the continued action of the EAAs on the AMPA and KA receptors.

NMDA, AMPA and KA are glutamic acid analogs as shown by the following schematics.

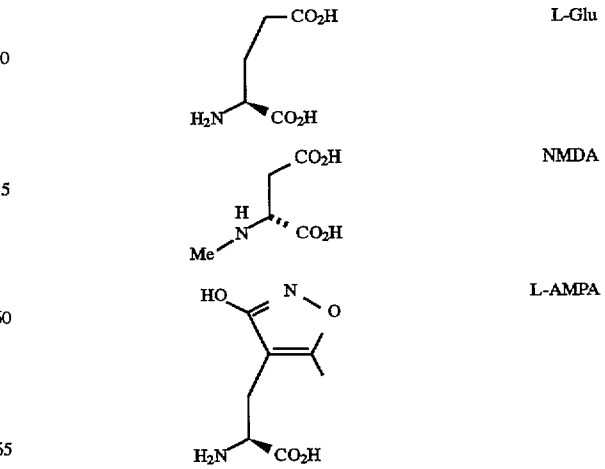

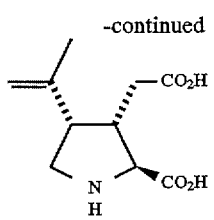
kainic acid

It is remarkable that these analogs can distinguish between receptor types and must reflect subtle differences in the three dimensional conformation of the various binding sites. Selective binding of conformationally restricted analogs suggests that glutamic acid may bind to each receptor in a distinct conformation. Glutamic acid itself has at least nine low energy staggered conformations. The existence of these distinctions also suggests a fine degree of chemical regulation exercised over the EAA receptors and the potential to find selective modulators of the receptors if the necessary binding conformations were understood for each receptor.

Originally isolated from the seaweed *Digenea simplex*, which grows off the coast of Japan, KA is a glutamic acid analog having three asymmetric carbon atoms. It is one of the most potent commonly used exogenous excitotoxins, and studies have shown that its neurotoxic action is mediated through the AMPA and KA receptors. Of particular interest is the fact that the neuronal degeneration caused by KA excitotoxicity differs significantly from that observed with other EAA receptor agonists. In fact, the degeneration seen in the brains of test animals after KA exposure is remarkably similar to that seen in the neurodegenerative disorder, Huntington's disease, and temporal lobe epilepsy.

While a great deal has been learned about the regulation of the NMDA receptor by allosteric modulators, much less is known about the AMPA and KA receptors. A principal reason for this lack of knowledge is that no compounds are known which selectively modulate the KA receptor. For example, 6-nitro-7-sulfamoylbenzo[f]quinoxaline-2,3-dione (NBQX) has been reported by Jacobsen, et al., in U.S. Pat. No. 4,889,855 to be an AMPA/KA receptor antagonist useful for treating neurodegenerative diseases. NBQX is the most AMPA/KA receptor selective member of the quinoxaline-2,3-dione family of compounds. Though NBQX competitively inhibits glutamate binding to both the AMPA and the KA receptors, it has an affinity thirty times greater for the AMPA receptor as compared to the KA receptor and also non-specifically binds to the glycine site of the NMDA receptor. Unfortunately, since NBQX has very limited solubility in water it has not been developed for human use. Thus, it has been impossible to study the effect of the EAA's on KA receptors without having an unknown contribution from the other receptors. In addition, it has been impossible to selectively prevent damage caused by excess EAA stimulation of the KA receptor. Clearly, the availability of compounds which selective modulate the KA receptor could prevent excitotoxic cell death due to excess stimulation.

Since the discovery that glutamic acid and aspartic acid are natural neurotransmitters that activate neuroreceptors, chemists and pharmacologists have attempted to understand the critical aspects of shape, pharmacophore position and pharmacophore type that are important for agonist or antagonist modulation of the receptors. Generally, random screening and hit or miss synthesis and testing were used to find new agonists or antagonists for the receptors. It is likely that each glutamic acid receptor subtype, such as NMDA, AMPA or KA, will have its own requirements for agonist shape and pharmacophore positions along with different shape and pharmacophore positions for antagonists. The optimal way to design new agonists or antagonists is to have an agonist or antagonist model for each receptor subtype that contains the specific shape and pharmacophore positions and then to use this model to link the pharmacophores into novel molecules.

Since glutamic acid is involved in many different biochemical reactions throughout the cell, attempts have been made to find glutamic acid analogs in which the stereochemistry about the various glutamic acid carbons has been altered in an attempt to find other molecules which would have the correct dimensional fit to participate in the biochemical reactions.

Several publications disclose substituted alkyl glutamic acids. H. J. Overman et al (*Neuroscience*, 26(1), 17–31, 1988, Table 4) describe racemic DL 4-methylglutamic acid, DL 4-fluoroglutamic acid or DL 3-methylaspartic acid and their binding to the NMDA receptor. Overman teaches that the methyl group is detrimental to NMDA binding affinity compared to glutamic acid itself.

Much of what has been learned about the NMDA receptor has been made possible by the discovery of compounds which block one or another action of the various modulatory agents. The approach of using blocking agents to map pathways has a long history in biochemical and biophysical research and very often these blocking agents have been discovered to be useful therapeutic agents. Compounds which selectively bind to the KA receptor are no exception.

It is therefore an object of the present invention to provide compounds which selectively bind to the KA receptor.

It is a further object of the present invention to provide compounds which selectively modulate or regulate the KA receptor function.

It is a further object of this invention to provide compounds and methods for use of the compounds to specifically regulate the flow of cations through the KA ligand-gated EAA receptor complex.

It is another object of the present invention to provide methods for designing glutamate receptor modulators.

It is still another object of the present invention to provide compounds and methods of use thereof for treatment of neurological, neuropsychological, neuropsychiatric and neuropsychopharmocological conditions, neurodegeneration after central nervous system or spinal trauma and injury, alleviation of pain, and enhancement of learning and memory.

A further object of the invention is to provide compounds and methods for use thereof to treat chemical toxicity in patients using compounds which selectively act at the KA receptor.

SUMMARY OF THE INVENTION

A class of alkyl carboxy amino acid compounds has been discovered which bind to the KA receptor and modulate the KA receptor function. Illustrative compounds include:

(2S,4R)-4-methyl glutamic acid, and (2S,4S)-4-methyl glutamic acid.

These compounds, in combination with suitable pharmaceutically acceptable carriers, are useful in methods to treat: 1) neurological, neuropsychological, neuropsychiatric, neurodegenerative, neuropsychopharmacological and functional disorders associated with excessive or insufficient activation of the Kainate subtype of the ionotropic EAA receptors; 2) cognitive disorders associated with deactivation, suboptimal activation, or over-activation of the KA receptor; 3) to improve and enhance memory, learning, and associated mental processes; and 4) alleviation of pain. The compounds can also be used as testing agents to identify and characterize other compounds for the treatment of acute and chronic neurodegenerative diseases, seizures, depression, anxiety and substance addiction.

A method of designing and screening for glutamate receptor agonists, partial agonists, partial antagonists, or antagonists on AMPA, KA, NMDA, metabotropic or other receptors, is also described, based upon the models characterized herein. Agonist binding shapes are derived from one of nine low energy conformations of glutamic acid. Low energy conformations are those conformations within three kcal of the global minimum energy conformation as calculated by a molecular mechanics program and force field such as the Universal 1.01 Force Field described by Rappé, *J. Amer. Chem. Soc.* 114, 10,024 (1992). The NMDA, AMPA and KA receptors each require a different shape of glutamic acid and positioning of the amino and carboxyl pharmacophores for the agonist conformation of the receptor.

Based on this model and the results shown in the examples, a compound that binds to the KA receptor with an $IC_{50}<50$ µM for inhibition of [$^3$H] kainic acid binding, has an amino group with hydrogens or a lone pair of electrons projecting as in FIG. 1, and oxygens $O^1$, $O^3$ and $O^4$ with lone pairs of electrons projecting as in FIG. 1, is an agonist for receptor function. A compound with an amino group and all oxygens $O^1$, $O^2$, $O^3$ and $O^4$ as in FIG. 1 has optimal agonist activity. A compound that binds to the KA receptor with an $IC_{50}<50$ µM for inhibition of [$^3$H] kainic acid binding, an amino group with hydrogens projecting as in FIG. 2 and oxygens with lone pairs of electrons projecting as in FIG. 2 is an antagonist for receptor function.

DETAILED DESCRIPTION OF THE INVENTION

Figure 1:
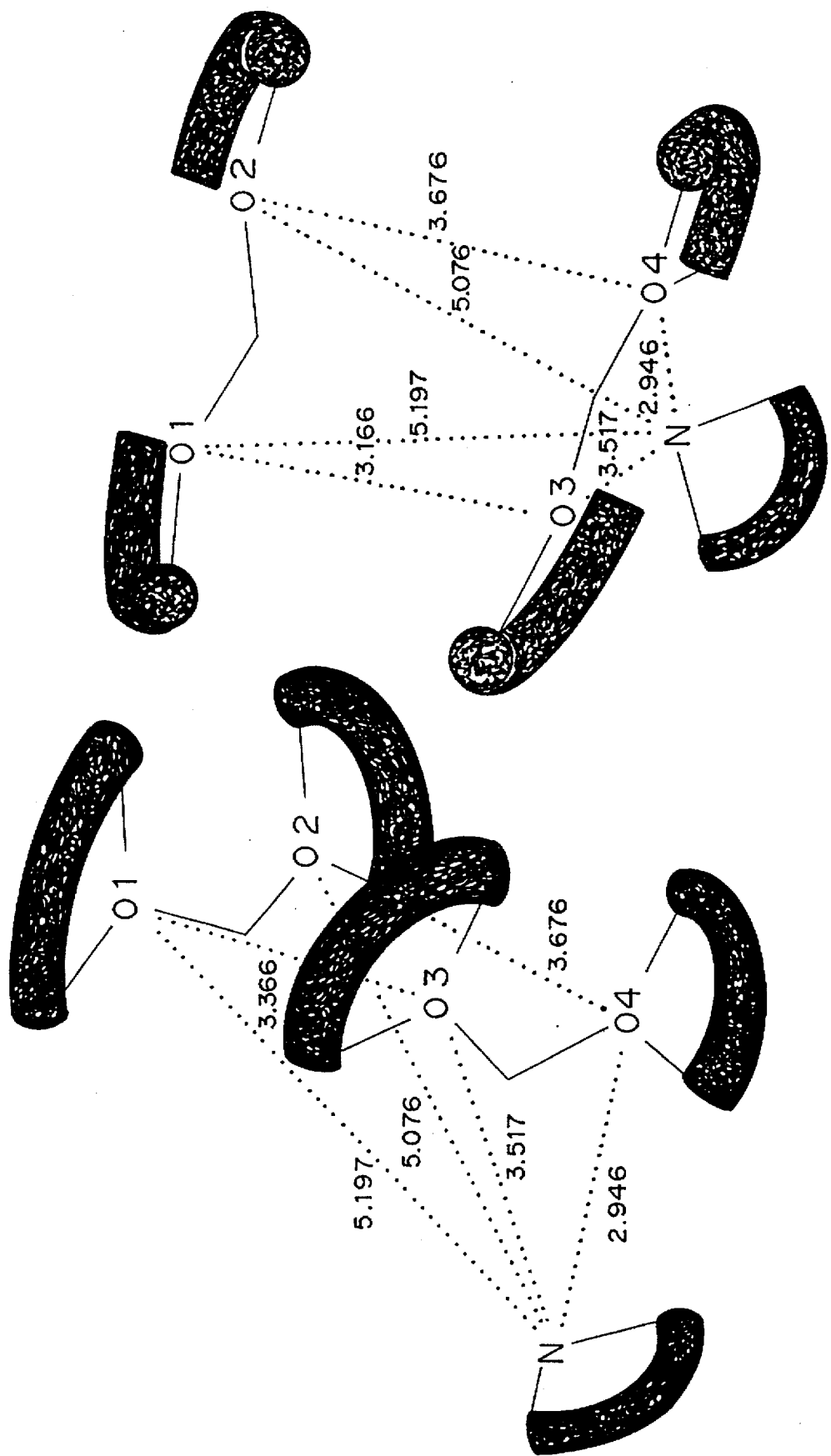
FIG. 1 is a schematic of two views of a KA agonist.
Figure 2:
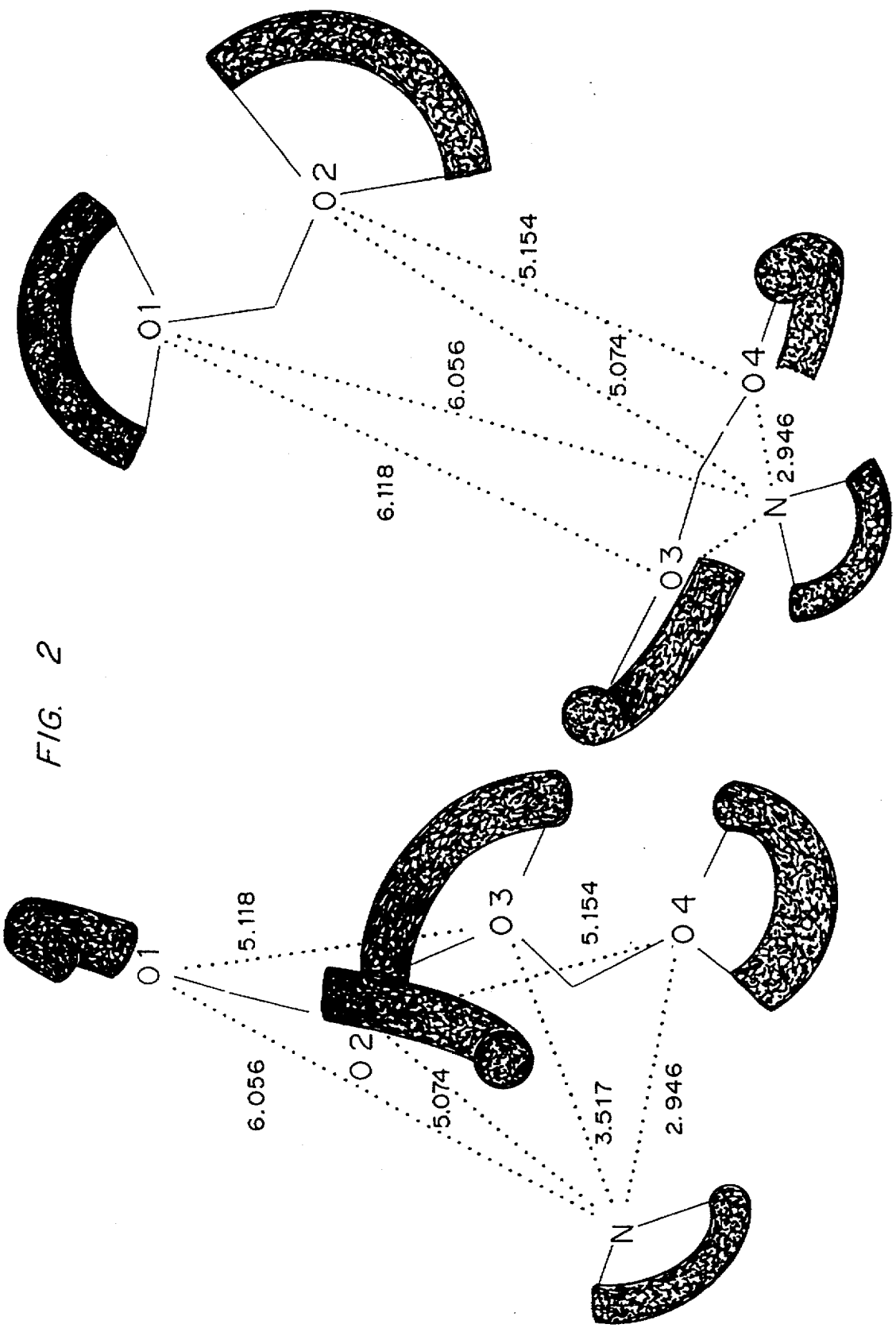
FIG. 2 is a schematic of two views of a KA antagonist.

I. Glossary of Terms.

The term "agonist" as used herein means any compound which increases the flow of cations through the Kainate receptor, that is, works as a channel opener, and which has not been observed to decrease the flow of cations through the same receptor.

The term "antagonist" as used herein means any compound which reduces the flow of cations through the Kainate receptor, that is, works as a channel closer, and which has not been observed to increase the flow of cations through the same receptor.

The term "partial agonist" as used herein means a compound which modulates an EAA receptor so as to increase or decrease the flux of cations through the ligand-gated channel depending on the presence or absence of the principal site modulator(s). In the absence of the principal site modulator(s), a partial agonist increases the flow of cations through the ligand-gated channel but at a lower flux than achieved by the principal site modulator(s). A partial agonist partially opens the receptor channel. In the presence of the principal site modulator(s), a partial agonist decreases the flow of cations through the ligand-gated channel below the flux normally achieved by the principal site modulator(s).

The term "principal site ligand" as used herein refers to known endogenous ligands binding to a site.

The term "glutamic acid" as used herein means the amino acid L-glutamic acid ("Glu").

The term "neuropsychopharmacological disorder" as used herein means a disorder resulting from, or associated with, a reduced or excessive flux of ions through the KA receptor ligand-gated cation channel, and includes cognitive, learning, and memory deficits, chemical toxicity (including substance tolerance and addiction), excitotoxicity, neurodegenerative disorder (such as Huntington's disease, Parkinson's disease, and Alzheimer's disease), post-stroke sequelae, epilepsy, seizures, mood disorders (such as bipolar disorder, dysthymia, and seasonal affective disorder), and depression. Neurodegenerative disorders can result from dysfunction or malfunction of the receptor. As used herein, this term includes pain.

The term "NMDA receptor" as used herein means a postsynaptic receptor which is stimulated, at a minimum, by the EAA glutamic acid as well as by NMDA, but is not stimulated by AMPA or kainic acid. It is a ligand-gated receptor.

The term "AMPA receptor" as used herein means a postsynaptic receptor which is stimulated by the EAAs glutamic acid as well as by AMPA, but is not stimulated by NMDA and only minimally and at high concentrations by kainic acid. It is a ligand-gated receptor.

The term "KA receptor" as used herein means a postsynaptic receptor which is stimulated, at a minimum, by the EAA glutamic acid as well as by KA, but is not stimulated by NMDA and only minimally and at high concentrations by AMPA. It is a ligand-gated receptor.

The term "potency" as used herein refers to the molar concentration at which a specified effect on a receptor channel is observed. Specifically, potency for a compound exhibiting antagonistic effect is presented as the $IC_{50}$ value, which is the concentration at which inhibition of channel opening is 50% of the maximum inhibition achievable. Lower values indicate higher potency. Potency for a compound exhibiting agonistic effect is presented as the $EC_{50}$ value, which is the concentration at which enhancement of channel opening is 50% that of the maximum enhancement achievable. Lower values indicate higher potency.

The term "efficacious" as used herein refers to a comparison of the maximum channel opening or closing achieved by a particular compound with maximum channel opening or closing achieved by a principal site ligand. Efficacy refers to magnitude of a specified effect.

The term "pharmacophore" as used herein means an atom or group of atoms that electrostatically or through hydrogen bonds interacts directly with the receptor protein.

The term "specifically binds" as used herein means a compound binding to a receptor with an affinity at least three times as great as a compound which binds to multiple sites or receptors.

When an alkyl substituent is identified herein, the normal alkyl structure is intended (i.e. butyl is n-butyl) unless otherwise specified. However, when radicals are identified (e.g. $R^1$), both branched and straight chains are included in the definition of alkyl, alkenyl, and alkynyl.

Pharmaceutically acceptable salts include both the metallic (inorganic) salts and organic salts; a list of which is given in Remington's Pharmaceutical Sciences 17th Edition, p. 1418 (1985). It is well known to one skilled in the art that an appropriate salt form is chosen based on physical and chemical stability, flowability, hydroscopicity and solubility.

Depending on the required activity, compounds from this class may be used as pharmaceutical neuroprotectants to treat acute cases of CNS injury and trauma as well as to treat convulsions, mood disorders, alleviation of pain, and other neuropsychiatric and neurodegenerative diseases due, in part, to chronic disturbances in the control of the ion flux through the KA receptor. Similarly, the compounds of this class can be selected for the required activity to treat the disorder. As used herein, the common definitions of neuropsychiatric and neurogenerative disorders are intended, where diagnosis is based on the alleviation of abnormal behavior, rather than histopathology.

II. Synthesis

A class of alkyl carboxy amino acid compounds has been discovered which bind to the KA receptor and modulate the KA receptor function. These compounds have the following formula:

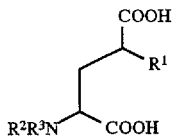

wherein:
R¹ is
1) CH₃, or
2) halogen (F, Cl, and Br);
R² and R³ are independently
1) H,
2) C1–C6-alkyl,
3) C3–C4-alkenyl,
4) C3–C5-cycloalkyl,
5) C1–C6-alkyl-CO—,
6) C1–C6-alkyl-OCO—,
7) C1–C6-alkyl-NHCO—,
8) HCO—, or
9) C3–C6-alkynyl;
R² and R³ taken together can be —CH₂(CH₂)$_p$CH₂—;
p is 0 to 3;
and pharmaceutically acceptable salts of these compounds.

Preferred compounds are compounds of Formula I wherein:
R¹ is CH₃;
R² and R³ are independently
1) H,
2) C1–C3-alkyl,
3) C3–C4-alkenyl,
4) C3-cycloalkyl,
5) HCO—, or
6) CH₃—(CH₂)$_n$—CO—;
R² and R³ taken together can be —CH₂(CH₂)$_p$CH₂—;
n is 0 to 1;
p is 0 to 3;
and pharmaceutically acceptable salts of these compounds.

More preferred of the preferred compounds are compounds of Formula I which selectively bind to the kainate receptor wherein:
R² and R³ are independently
1) H,
2) C1–C3-alkyl,
3) HCO—, or
4) CH₃—CO—;
and pharmaceutically acceptable salts of these compounds.
Illustrative compounds include:
(2S,4R)-4-methyl glutamic acid,
(2S, 4S)-methyl glumatic acid,
(2R, 4S)-methyl glumatic acid, and
(2R, 4R)-methyl glumatic acid.

The compounds of Formula I my be prepared using the reactions and techniques described in this section. The reactions are performed in solvents suitable to the reagents and materials employed and suitable for the transformation being effected. It is understood by those skilled in the art of organic synthesis that the functionality present on the molecule must be consistent with the chemical transformations proposed. This will frequently necessitate judgment as to the order of synthetic steps, protecting groups required, deprotection conditions and generation of enolate ions to enable attachment of appropriate groups on the molecule.

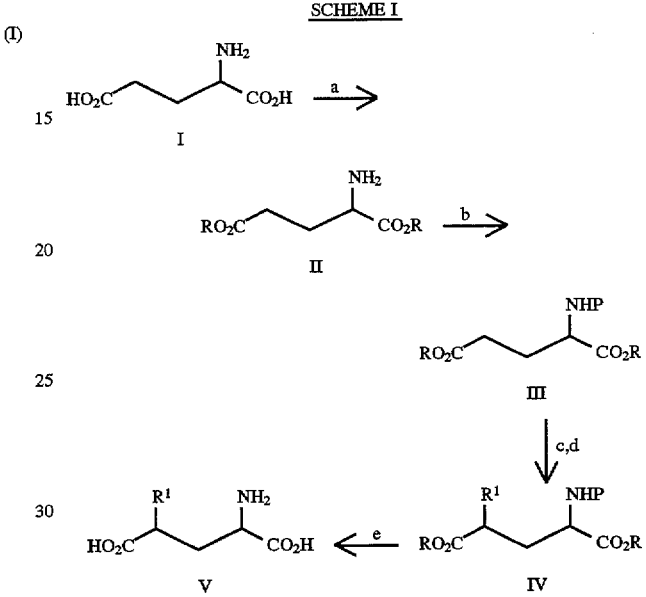

a) 1. SOCl₂ or (ClCO)₂, 2. ROH.
b) 4-Nitrobenzoyl chloride, CH₂Cl₂, or 20% aqueous Na₂CO₃ or 2-Naphthoyl chloride, CH₂Cl₂, Et₃N.
c) LiN(SiMe₃)₂, THF
d) Rx In Scheme I, (S)- or (R)-glutamic acid is esterified under standard conditions (March, "Advanced Organic Chemistry", 4th Edition 1992, Wiley-Interscience Publication, New York) with an appropriate alcohol, such as methanol, ethanol, t-butanol or benzyl alcohol. The amine group of the diester product, Formula II, is then protected under standard conditions, Buehler and Pearson, "Survey of Organic Synthesis", 1970, Wiley-Interscience Publication, New York, by an appropriate amine protecting group, such as an aromatic amide such as nitrobenzoyl, naphthoyl, N-tert-butoxycarbonyl (BOC) or carbobenzyloxy (CBZ). The enolate of this fully protected glutamic acid, III, is prepared by reacting III with a strong base, such as lithium bis(trimethylsilyl)amide or lithium diisopropylamide, in an inert solvent, such as tetrahydrofuran or ethyl ether, at a temperature range of –78° to 0° C. for 1 to 5 hr. The enolate is then reacted with an electrophile such as an alkylhalide, at a temperature between –78° to –30° C. for 0.5 to 24 hr to afford compounds of Formula IV. If the starting glutamic acid has the (2S) stereochemistry, the product has the (2S,4S) stereochemistry. Conversely if the starting glutamic acid has the (2R) stereochemistry, the product has the (2R,4R) stereochemistry. The compounds described herein wherein R¹ are alkyl, alkenyl, alkynyl, and cycloalkyl are prepared from this procedure. The compound of Formula V is prepared by reacting the compound of Formula IV with a strong aqueous acid such as HCl at a temperature of 0° C. to reflux for 1 to 48 hr or by treatment with LiOH in a solvent such as THF or ethanol at a temperature of 0° C. to 60° C. for 0.5 to 18 hr, then treatment with trifluoracetic acid in a solvent such as methylene chloride (CH$_2$Cl$_2$) at room temperature for 0.5 to 24 hr.

SCHEME II

CH$_3$CONHCH(CO$_2$CH$_2$CH$_3$)$_2$

VI

+

$\xrightarrow{f}$

CH$_2$=C(R$^1$)CO$_2$CH$_3$

VII

CH$_3$CONHC(CO$_2$CH$_2$CH$_3$)$_2$CH$_2$CH(R$^1$)CO$_2$CH$_3$

VIII

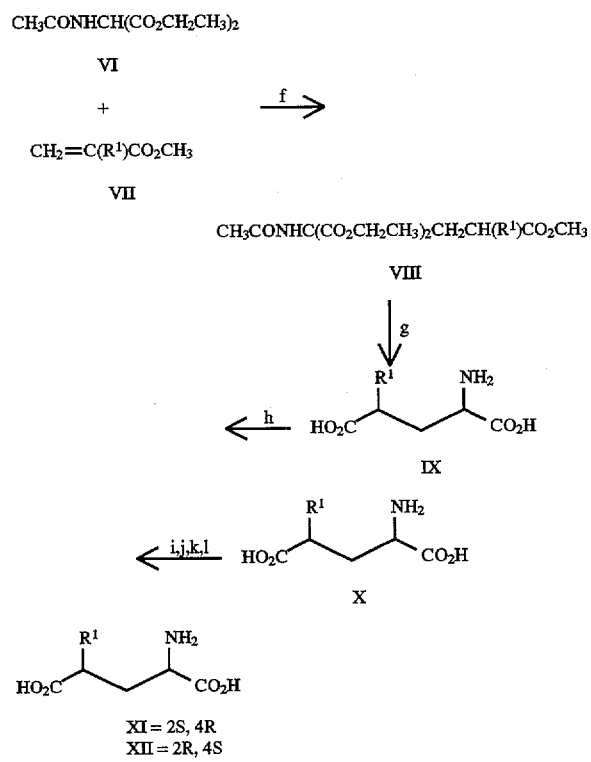

XI = 2S, 4R
XII = 2R, 4S f) Na, CH$_3$CH$_2$OH
g) 20% HCl
h) fractional crystallization
i) 1. SOCl$_2$, 2. ROH
j) (−)-MTPC or (+)-MTPC, CH$_2$Cl$_2$, 20% NaCO$_3$
k) separation
l) 6N HCl The compounds of Formulas IX, X, XI and XII can be prepared according to Scheme II. Compounds of Formula IX, which are a diastereomeric mixture, can be prepared by the procedure described in "Chemistry of Amino Acids", Ed. J. P. Greensein and M. Winitz, Vol. 3, 1984; Kreiger Publishing: Malabar, Fla., pp. 2438–2445 and references cited therein. The racemic diacid compounds of Formula X (2S, 4R) and (2R, 4S), obtained by fractional crystallization, can then be separated into the individual stereoisomers by standard physical or chemical procedures as described in March, "Advanced Organic Chemistry", 4th Edition 1992, Wiley-Interscience Publication, New York, and references cited therein. As an example, the compounds of Formula X can be esterified under the standard conditions described above and then the amine acylated with a chiral acylating agent, such as (R)-(+)- or (S)-(−)-α-methoxy-α-(trifluoromethyl) phenylacetyl chloride in an inert solvent, such as CH$_2$Cl$_2$, with an amine base present, such as triethylamine, pyridine or N,N-dimethylamino-pyridine, at a temperature of 0° C. to reflux of the solvent for 0.5 to 24 hr. The resulting diastereomers can then be physically separated by fractional crystallization or chromatography and then the protected chiral isomers can be deprotected by reacting with a strong aqueous acid such as HCl at a temperature of 0° C. to reflux for 1 to 48 hr. to give individual isomers such as the compounds of Formulas XI or XII.

Alternatively XI and XII can be prepared by the procedures outlined in Scheme III. The intermediate XIV can be prepared by the procedures described by Woo and Jones (Tel. Lett. 32(47), 6949–6952, 1991). Pyroglutamic acid can be esterified under standard conditions (March, "Advanced Organic Chemistry", 4th Edition 1992, Wiley-Interscience Publication, New York) with an appropriate alcohol, such as methanol, ethanol, t-butanol or benzyl alcohol to give XIII. The ester XIII is then reduced with a reducing agent such as NaBH$_4$ in an alcohol solvent such as ethanol ("EtOH") at 0° C. to room temperature for 1 to 24 hr. The corresponding alcohol is then silylated with a reagent such as (t-Bu) Ph$_2$SiCl in an inert solvent such as THF or methylene chloride at 0° C. to room temperature for 1 to 24 hr. The amide is then protected with an amino acid protecting group such as BOC by treatment with BOCCl or (BOC)$_2$O and a base such as pyridine or Et$_3$N in an inert solvent such as CH$_2$Cl$_2$ at −10° C. to room temperature for 1 to 6 hr. The enolate of XIV is prepared by reacting XIV with a strong base, such as lithium bis(trimethylsilyl)amide or lithium diisopropylamide, in an inert solvent, such as tetrahydrofuran or ethyl ether, at a temperature range of −78° to 0° C. for 1 to 5 hr. The enolate is then reacted with an electrophile such as an alkylhalide, at a temperature between −78° to 30° C. for 0.5 to 24 hr to afford compounds of Formula XV. XV is then converted to the acid XVI by first deprotecting the alcohol by treatment with F in an inert solvent such as THF at room temperature then the alcohol is oxidized with an oxidizing agent such as RuCl$_3$/NaIO$_4$.

SCHEME III

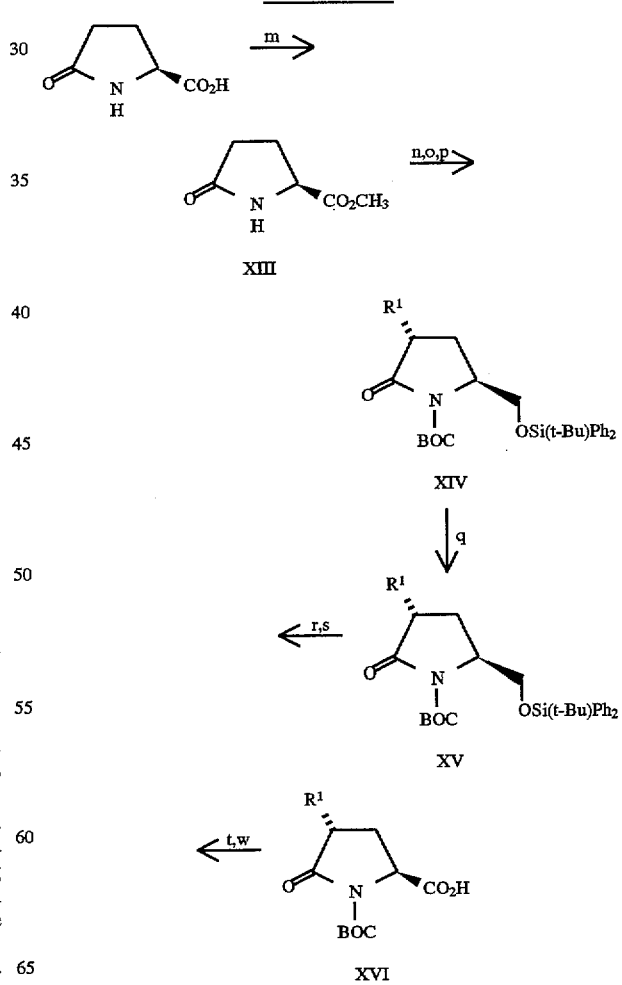

11

-continued
SCHEME III

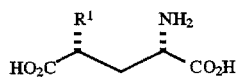

XI = 2S, 4R m) 1. $SOCl_2$, 2. MeOH;
n) $NaBH_4$, EtOH;
o) (t-Bu)$Ph_2$SiCl;
p) BOCCl;
q) 1. LiN(SiMe$_3$)$_2$, THF −78° C., 2. $R^1$X X = halogen
r) Bu$_4$F, THF;
s) $NaIO_4$/$RuCl_3$, CN/$H_2$O/$CCl_4$;
t) LiOH, THF/$H_2$O;
w) TFA, $H_2$O The compounds of Formula XVII can be prepared by acylation of the appopriately protected amino acid as described in Scheme IV, part a. The amino acid can be treated with an acylating agent, such as an acyl halide or an anhydride, in an inert solvent such as toluene or $CH_2Cl_2$ with a base, such as pyridine or N,N-dimethylaminopyridine or in a mixed solvent system such as toluene/water with a base such as NaOH or $Na_2CO_3$ at a temperature of 0° C. to reflux of the solvent. Deprotection of the product under the appropriate conditions would give XVII.

The compounds of Formula XVIII can be prepared by formylation of the appropriately protected amino acid as described in Scheme IV, part b. The amino acid can be treated with a formylating agent, such as a mixed anhydride, in an inert solvent such as toluene or $CH_2Cl_2$ with a base, such as pyridine or N,N-dimethylaminopyridine or in a mixed solvent system such as toluene/water with a base such as NaOH or $Na_2CO_3$ at a temperature of 0° C. to reflux of the solvent. Deprotection of the product under the appropriate conditions would give XVIII.

The compounds of Formula XIX and XX can be prepared by alkylation of the appropriately protected amino acid as described in Scheme IV, part c. The amino acid can be reductively mono- or bis-alkylated by treatment with the desired aldehyde such as acetaldehyde and a reducing agent such as $NaBH_3CN$ in a solvent such as acetic acid at a temperature of between 20° C. and 80° C. Deprotection of the product under the appropriate conditions would give XIX and XX.

The compounds of Formula I where Y is heterocyclic can be prepared by modifications known to one skilled in the art

12 of the procedures described in EPA 590,789 by Eli Lilly and the references therein.

The compounds described herein and their preparation will be understood further from the following non-limiting examples. In these examples, unless otherwise indicated, all temperatures are in degrees Celsius and parts and percentages are by weight.

A variety of analogs of glutamic acid were synthesized, in particular, analogs of 4-alkyl-substituted glutamate. 4-methylglutamate has two chiral centers, resulting in four stereoisomers, as synthesized and isolated below.

EXAMPLE 1

(2R, 4R)-4-Methyl Glutamic Acid

PART A: Preparation of N-(4-Nitrobenzoyl) R-Glutamic Acid Diethyl Ester

To a solution of 14.7 g (100 mmol) of D-glutamic acid in 150 mL of ethanol cooled to 0° C., 11 mL (150 mmol) of thionyl chloride was added dropwise. The mixture was then heated until it became clear. The reaction mixture was then allowed to stir at room temperature for 48 hr. After evaporating the solvent, a clear oily residue was obtained which was carried on to the next step. The oily residue and 18.5 g (100 mmol) of 4-nitrobenzoyl chloride was stirred in 150 mL of methylene chloride and 20 mL of water. A 100 mL of 20% $Na_2CO_3$ solution was slowly added. The reaction mixture was allowed to stir at room temperature for 3 hr. The organic phase was separated and after evaporating the solvent, the residue was crystallized from diethyl ether. m.p. 90°–92° C.; $^1$H-NMR (200 MHz, CDCl$_3$): δ 1.25 (t, J=7.2 Hz, 3H), 1.30 (t, J=7.2 Hz, 3H), 2.25 (m, 2H); 2.50 (m, 2H); 4.12 (q, J=7.1 Hz, 2H); 4.22 (q, J=7.1 Hz, 2H); 7.5 (d, J=7.1 Hz), 8.00 (dd, J=2.0, 6.9 Hz, 2H); 8.30 (dd, J=1.9, 6.9 Hz, 2H).

PART B: Preparation of N-(4-nitrobenzoyl) (2R,4R)-4-Methyl Glutamic Acid Diethyl Ester To a solution of 3.52 g (10 mmol) of N-(4-nitrobenzoyl)-D-glutamic acid diethyl ester in 100 mL of anhydrous tetrahydrofuran which was cooled to −78° C. under nitrogen, 22 mL (22 mmol) of 1.0M solution of lithium bis (trimethylsilyl)amide in THF was slowly added via syringe. The mixture was stirred at −78° C. for 1 hr, then 40 mmol

SCHEME IV

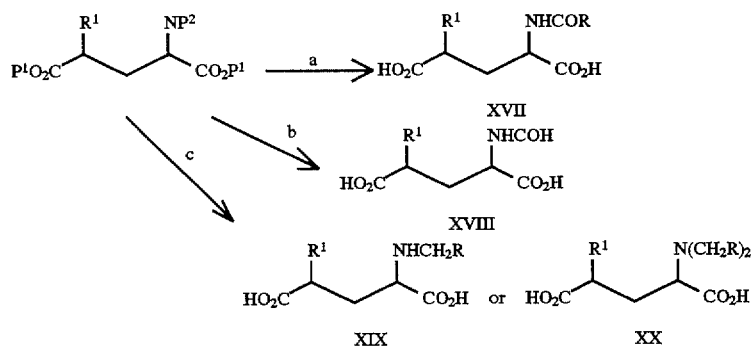

a) RCOCl, pyr or RCOCl, $CH_2Cl_2$, 20% $Na_2CO_3$
b) $HCO_2H$, $Ac_2O$
c) RCHO, $NaBH_3Cn$ of iodomethane was added. The reaction mixture was then quenched with saturated ammonium chloride. After evaporating half of the solvent, the mixture was diluted with 200 mL of water and extracted with methylene chloride (3 X 50 mL). The combined extracts were washed with water, brine, and dried over MgSO$_4$. The solvent was evaporated and the oily residue purified through a column of silica gel, eluting with a mixture of ethyl acetate and hexanes (1:1) to yield 1.6 g of oil. $^1$H-NMR (200 MHz, CDCl$_3$): δ 1.25 (m, 9H), 2.12 (m, 2H), 2.6 (m, 1H), 4.2 (m, 4H), 4.80 (m, 1H), 6.95 (d, J=7.8 Hz, 1H), 8.0 (d, J=8.0 Hz, 2H), 8.3 (d, J=8.0 Hz, 2H).

PART C: Preparation of (2R,4R)-4-Methyl Glutamic Acid

The product B above was refluxed in 50 mL of 6N HCl for 2 hr. and then cooled to room temperature. The precipitate was filtered and the filtrate was concentrated in vacuo. The residue was dissolved in 50 mL of distilled water and washed with 50 mL of 5% of trioctylamine in chloroform twice. The aqueous phase was concentrated in vacuo and the oily residue crystallized in acetone and water. m.p. 190°–192° C.; $^1$H-NMR (200 MHz, D$_2$O): δ 1.24 (d, J=7.1 Hz, 3H); 2.05 (m, 1H); 2.2 (m, 1H), 2.80 (m, 1H); 4.07 (dd, J=6.3, 7.9 Hz, 1H).

EXAMPLE 2

(2S,4S)-4-Methyl Glutamic Acid

Using appropriate starting materials, the (2S,4S)-4-methyl glutamic acid was obtained by using the procedures described in Parts B and C of Example 1. m.p. 179°–182° C.; $^1$H-NMR (200 MHz, D$_2$O): δ 1.24 (d, J=7.1 Hz, 3H); 2.05 (m, 1H); 2.2 (m, 1H), 2.80 (m, 1H); 4.07 (dd, J=6.3, 7.9 Hz, 1H).

EXAMPLE 3

(2S,4S), (2R,4R), (2S,4R), and (2R,4S)-4-Methyl Glutamic Acid Mixture

Sodium metal (500 mg) in small pieces was dissolved in 450 mL of absolute ethanol, and to this solution 400 mg of sulfur and 37 g (170 mM) of diethyl acetamidomalonate were added. Then 30 g (300 mM) of methyl methacrylate was added dropwise over a 4 hr period while refluxing. The reaction mixture was refluxed for another hour. The solvent was removed by evaporation in vacuo and the residue crystallized from ethanol to afford 33.4 g (62%) solid with m.p. 107°–109° C. 5 g (15.8 mmol) of this solid material was refluxed in 20% HCl for 2 hr then the solvent removed by evaporation in vacuo. The residue was dissolved in 50 mL of distilled water and washed with 5% of trioctylamine in CHCl$_3$. The aqueous phase was evaporated in vacuo and the oily residue dissolved in a very small amount of water (~1 mL) and crystallized with an excess of acetone to afford 1.3 g (54%) of the title compound with m.p. 163°–164° C.; $^1$H-NMR (300 MHz, D$_2$O): δ 1.17 (d, J=7.1 Hz, 1.5H), 1.18 (d, J=7.1 Hz, 3H), 1.83 (m, 1H), 1.95 (m, 0.5H), 2.1 (m, 0.5H), 2.25 (m, 0.5H), 2.65 (m, 1H), 3.85 (dd, J=6.5, 6.7 Hz, 1.5H). $^{13}$C-NMR (300 MHz, D$_2$O): δ 19.7, 19.8, 36.2, 36.4, 38.8, 38.9, 54.7, 54.9, 175.4, 182.5.

EXAMPLE 4

(2R,4S) and (2S,4R)-4-Methyl Glutamic Acid (2R,4S) and (2S,4R)-4-Methyl glutamic acid were obtained by fractional crystallization in water and acetone at 4° C. from racemic diastereomers obtained in Example 3. $^1$H-NMR (300 MHz, D$_2$O): δ 1.18 (d, J=7.0 Hz, 3H), 1.83 (m, 1H), 2.25 (m, 1H), 2.65 (m, 1H), 3.85 (dd, J=6.5, 6.8 Hz, 1H); $^{13}$C-NMR (300 MHz, D$_2$O): δ 19.8, 36.3, 38.8, 55.0, 175.6, 182.5.

EXAMPLE 5

(2S,4R)-4-Methyl Glutamic Acid (Scheme III)

Part A: (S)-1-t-Butoxycarbonyl-5-t-butyldiphenylsiloxymethyl-pyrrolidine-2-one

The title compound was prepared using literature procedures from (S)-(−)-2-pyrrolididone-5-carboxylic acid. mp=108°–109° C. $^1$H NMR (200 MHz, CDCl$_3$): δ 7.62 (m, 5H), 7.40 (m, 5H), 4.20 (m, 1H), 3.88 (dd, J=10.4, 4.1 Hz, 1H), 3.70 (dd, J=10.4, 2.5 Hz, 1H), 2.80 (m, 1H), 2.45 (m, 1H), 1.75 (m, 1H), 2.10 (m, 2H), 1.42 (s, 9H), 1.05 (s, 9H).

PART B: (3R,5S)-1-t-Butoxycarbonyl-5-t-butyldiphenylsiloxymethyl-3-methyl-pyrrolidine-2-one To a solution of (S)-1-t-butoxycarbonyl-5-t-butyldiphenylsiloxymethyl-pyrrolidine-2-one (15 g, 33 mmol) in THF (250 mL) at −78° C. a 1M solution of LiN(SiMe$_3$)$_2$ (35 mL, 35 mmol) was slowly added. After stirring for 1 hr, iodomethane (6.2 mL, 100 mmol) was added. The reaction mixture was allowed to stir for another 2 hr at −78° C. and then quenched with acetic acid. The mixture was concentrated into half volume, diluted with water (200 mL) and extracted with ethyl acetate (EtOAc). The combined extracts were washed with water, brine and dried over MgSO$_4$. The solvent was evaporated in vacuo and the residue purified by flash column chromatography on silica gel, eluted with EtOAc:Hexane (1:2.5). The desired (2S,5R) isomer was eluted first from the column and crystallized in hexanes to give 7.3 g (47%) of product as white crystals. mp=84°–85° C. $^1$H NMR (200 MHz, CDCl$_3$): δ 7.62 (m, 5H), 7.40 (m, 5H), 4.12 (m, 1H), 3.85 (dd, J=10.3, 4.7 Hz, 1H), 3.72 (dd, J=10.3, 2.8 Hz, 1H), 2.82 (m, 1H), 2.31 (dd, J=12.7, 8.9 Hz, 1H), 1.75 (m, 1H), 1.42 (s, 9H), 1.20 (d, J=7.0 Hz, 3H), 1.02 (s, 9H).

Part C: (3R,5S)-1-t-Butoxycarbonyl-5-hydroxymethyl-3-methylpyrrolidine-2-one

To a solution of (3R,5S)-1-t-butoxycarbonyl-5-t-butyldiphenylsiloxymethyl-3-methyl-pyrrolidine-2-one (17.8 g, 38.1 mmol) and glacial acetic acid (2 eq) in dry THF (50 mL) at 0° C. was added a 1.0M solution of tetrabutylammonium fluoride in THF (150 mL, 150 mmol). The solution was allowed to warm room temperature and stir overnight. Ethyl acetate (500 mL) was added and the organic phase extracted with aqueous ammonium chloride (20%, 3 x 200 mL). The combined aqueous phases were extracted with ethyl acetate (200 mL). The combined organic phases were washed with brine (500 mL), dried over Na$_2$SO$_4$, filtered and evaporated to dryness. The crude product was purified by filtration through silica gel, eluted with 70% EtOAc in hexane to give the product as a clear oil, which was carried on for next step without further characterization.

Part D: (3R,5S)-1-t-Butoxycarbonyl-5-carboxy-3-methylpyrrolidine-2-one

To a solution of (3R,5S)-1-t-butoxycarbonyl-5-hydroxymethyl-3-methylpyrrolidine-2-one in a solvent mixture of acetonitrile:carbon tetrachloride:water (2:2:3, 266 mL) was added sodium periodate (3 eq, 24.0 g) and ruthenium trichloride (2.2 mol %, 0.174 g). The solution was stirred 2 hr at room temperature and then diluted by the addition of dichloromethane (500 mL) and brine (200 mL). The organic phase was separated and the aqueous phase was extracted with dichloromethane (3 x 200 mL). The combined organic phases were dried over $Na_2SO_4$ then celite added. The solution was filtered under suction through a bed of celite and the filtrate was evaporated to give an oily residue which was crystallized in ethyl acetate and hexane to give 5.03 g product (54%). The mother liquor was purified by flash column chromatography on silica gel, eluting with 70% ethyl acetate in hexane (with 1% of formic acid) to give an additional 1.21 g (13%) of the acid (total 67% yield in two steps). $^1$H NMR (200 MHz, $CDCl_3$): δ 6.65 (br s, 1H), 4.60 (d, J=8.6, 0.9 Hz, 1H), 2.70 (m, 1H), 2.40 (dd, J=12.5, 8.8 Hz, 1H), 2.0 (m, 1H), 1.55 (s, 9H), 1.25 (d, J=7.0 Hz, 3H).

Part E: (2S,4R)-N-t-Butoxycarbonyl-4-methyl glutamic acid

A solution of (3R,5S)-1-t-Butoxycarbonyl-5-carboxy-3-methylpyrrolidine-2-one (6.2 g, 25.5 mmol) in THF (50 mL) was treated with lithium hydroxide monohydrate (3 eq, 3.20 g) and water (5 mL). After stirring for 16 hr at room temperature the THF was removed in vacuo and water (20 mL) was added. The pH was adjusted to 3 by the addition of glacial acetic acid, ether (100 mL) was added and the layers separated. The aqueous phase was extracted with ether (3 x 100 mL) and the combined organic phases were washed with brine (400 mL), dried over $Na_2SO4$, filtered and evaporated to dryness, azeotroping with toluene (3 x 15 mL). The residue was dried under high vacuum to give 6.58 g of the product (99%) as a white foam which was used without further purification: $R_f$ 0.8 (1% formic acid in ethyl acetate, developed with ninhydrin). $^1$H NMR (200 MHz, $D_2O$): δ 3.80 (dd, J=10.4, 4.7 Hz, 1H), 2.45 (m, 1H), 2.0 (m, 1H), 1.60 (ddd, J=12.8, 4.2, 10.3 Hz, 1H), 1.25 (s, 9H), 1.0 (d, J=7.0 Hz, 3H).

Part F: (2S, 4R)-4-Methyl Glutamic Acid

The Boc-protected diacid, (2S, 4R)-N-t-butoxycarbonyl-4-methyl glutamic acid, was subjected to a mixture of trifluoroacetic acid:methylene chloride (40:60, 100 mL) for 3 hr at room temperature. The volatiles were removed in vacuo and the residue was azeotroped with toluene (50 mL). Water (150 mL) was added and the aqueous phase extracted with a 5% solution of trioctylamine in chloroform (3 x 200 mL). The combined organic phases were washed with water (50 mL) and the combined aqueous phases evaporated by being placed on a lyophilizer for 48 hr to give the product (4.6 g, 66% in two steps) as a white foam which was recrystallized in acetone and water. mp=169°–170° C., $^1$H NMR (200 MHz, $D_2O$): δ 3.80 (dd, J=7.3, 7.3 Hz, 1H), 2.55 (m, 1H), 2.15 (ddd, J=14.7, 8.7, 6.6 Hz, 1H), 1.75 (ddd, J=14.6, 7.4, 5.4 Hz, 1H), 1.05 (d, J=7.0 Hz, 3H). Anal. Calculated for $C_6H_{11}NO_4$: C, 44.71; H, 6.88; N, 8.69. Found: C, 44.59; H, 6.85; N, 8.61.

Examples shown in Table 1 were prepared or can be prepared by the methods outline in Schemes I–IV presented above and procedures described in the Examples using the appropriate starting materials and reagents.

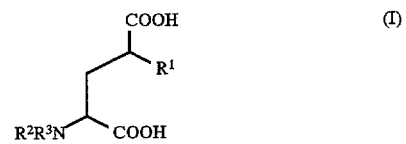

TABLE 1

| | Exemplary Compounds of Formula 1 | | | |
|---|---|---|---|---|
| Ex. | $R^1$ | $R^2, R^3$ | Stereo Config. | Anal. |
| 1 | —$CH_3$ | H, H | 2R, 4R | mp 115–118° C. |
| 2 | —$CH_3$ | H, H | 2S, 4S, | mp 179–182° C. |
| 3 | —$CH_3$ | H, —$CH_3$ | 2R, 4R | |
| 4 | —$CH_3$ | H, —CHO | 2R, 4R | |
| 5 | —$CH_3$ | H, —$COCH_3$ | 2R, 4R | |
| 6 | —$CH_3$ | H, H | 2S, 4S & 2R, 4R & 2S, 4R & 2R, 4S | mp 163–164° C. |
| 7 | —$CH_3$ | H, H | 2R, 4S & 2S, 4R | NMR |
| 8 | —$CH_3$ | H, H | 2S, 4R | mp 169–170° C. |
| 9 | —$CH_3$ | H, H | 2R, 4S | NMR |
| 10 | —$CH_3$ | —$CH_{3, H}$ | 2R, 4S 2S, 4R | |
| 11 | —$CH_3$ | —$CH_{3, H}$ | 2S, 4R | |
| 12 | —$CH_3$ | —$CH_{3, H}$ | 2R, 4S | |

III. Computer Modeling Method for Design of Compounds

Models were developed using Molecular Simulations Inc. Cerius2® 1.5 software on a Silicon Graphics Indigo II workstation. The model was constructed based on the structure of six known agonists of the KA receptor, KA, HFPA, Acromelic acids A and B, L-CCG-III, and L-CCG-IV, and two modulators, shown in Example 2 and (2S, 4S)-4-ethyl glutamic acid, and their respective $IC_{50}$'s for inhibiting [3H]kainic acid binding, shown in Table 2.

Figure 3:
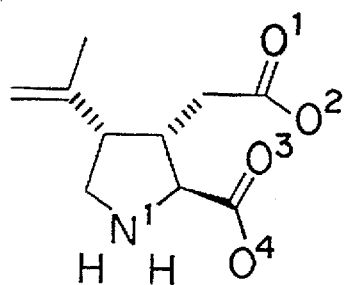
FIG. 3 is a schematic of a Pharmacophore Model.

Individual model agonists were analyzed with all carboxylic acids deprotonated and the basic amine protonated and minimized using the Universal Forcefield without a coulombic or hydrogen bond contribution to the overall energy. The global minima were aligned using the basic amine $N^1$ and the carboxyl oxygens $O^1$, $O^2$, $O^3$ and $O^4$ as overlapping pharmacophore constraints, as shown in the Pharmacophore Model in FIG. 3. Those compounds that did not align satisfactorily on kainic acid constraints were adjusted by deleting the $O^2$ overlap constraint.

TABLE 2

In Vitro Binding Assays at Glutamate Receptors in Rat Brain.

| Structure | Activity (nM)* | Predicted (nM) | Residual (nM)** | $E_{inside}$ | $E_{interact}$ | $E_{strain}$ | logP |
|---|---|---|---|---|---|---|---|
| HFPA | 8.22 | 8.11 | +0.11 | 39.937 | −104.942 | 62.025 | −1.320 |
| kainic acid | 7.92 | 7.89 | +0.03 | 38.946 | −107.775 | 44.499 | −1.345 |
| Acromelic acid B | 6.93 | 6.93 | +0.00 | 14.320 | −119.345 | 68.632 | −5.650 |
| Acromelic acid A | 6.48 | 6.36 | +0.12 | −2.992 | −115.594 | 56.197 | −6.35 |
| L-CCG-IV | 5.78 | 6.10 | −0.316 | −27.917 | −98.480 | 20.901 | −3.290 |
| Ex. 2 | 5.52 | 5.72 | −0.20 | −82.725 | −94.053 | 62.188 | −2.850 |
| (2S,4S)-4-ethyl glutamic acid | 4.92 | 4.72 | +0.20 | −114.021 | −89.177 | 13.197 | −2.320 |
| L-CCG-III | 4.59 | 4.53 | +0.06 | −122.706 | −63.174 | 29.249 | −3.290 |
| L-glutamic acid | 6.52 | 6.70 | −0.18 | −5.523 | −94.286 | 39.678 | −3.250 |
| AMPA | 4.00 | 3.93 | +0.07 | −57.321 | 1334.77 | 24.322 | −2.910 |

*Activity is measured as the actual inhibition of [3H]kainic acid binding to the Kainate Receptor, −log ($IC_{50}$ kainate binding).
**Residual is measured as the difference between the actual and predicted binding to the Kainate Receptor.

A pseudo-receptor surface was constructed from the four most potent agonists (HFPA, KA, and Acromelic acid A and B) and four less potent compounds (Example 2, (2S, 4S)-4-ethyl glutamic acid, L-CCGIII and L-CCGIV). A pseudo-receptor surface is formed as the hypothetical outer Van der Waals radii from one or a series of molecules that describes the combined three-dimensional properties of the molecule or molecules. This method constructs the pseudo-receptor surface based on the structure of each of the eight compounds, weighting the respective contribution of each structure based on the relative binding affinities of the agonists (expressed as -log($IC_{50}$) for inhibiting [$^3$H] kainic acid binding)). The surface fit to the chosen compounds was allowed to vary from the combined Van der Waals radii, to this distance plus 0.025 nm. The interaction or fit of the eight compounds with the pseudo-receptor surface was evaluated employing all energy terms. The interaction was evaluated in terms of $E_{inside}$, $E_{relax}$, $E_{strain}$ and $E_{interact}$. A QSAR table was constructed using the above described terms and a range of other calculated physical properties of the individual molecules, shown in Table 2. A genetic algorithm analysis of this data revealed a good correlation of the binding affinity ($IC_{50}$) as described above with $E_{interact}$, $E_{inside}$ and logP (partition coefficient). The equation generated is:

$$\text{Predicted} = 6.845 + 0.19 \, \text{Log}P + 0.017 \, E_{inside} - 0.0012 \, E_{interact} + 0.012 \, E_{strain}$$

Figure 4:
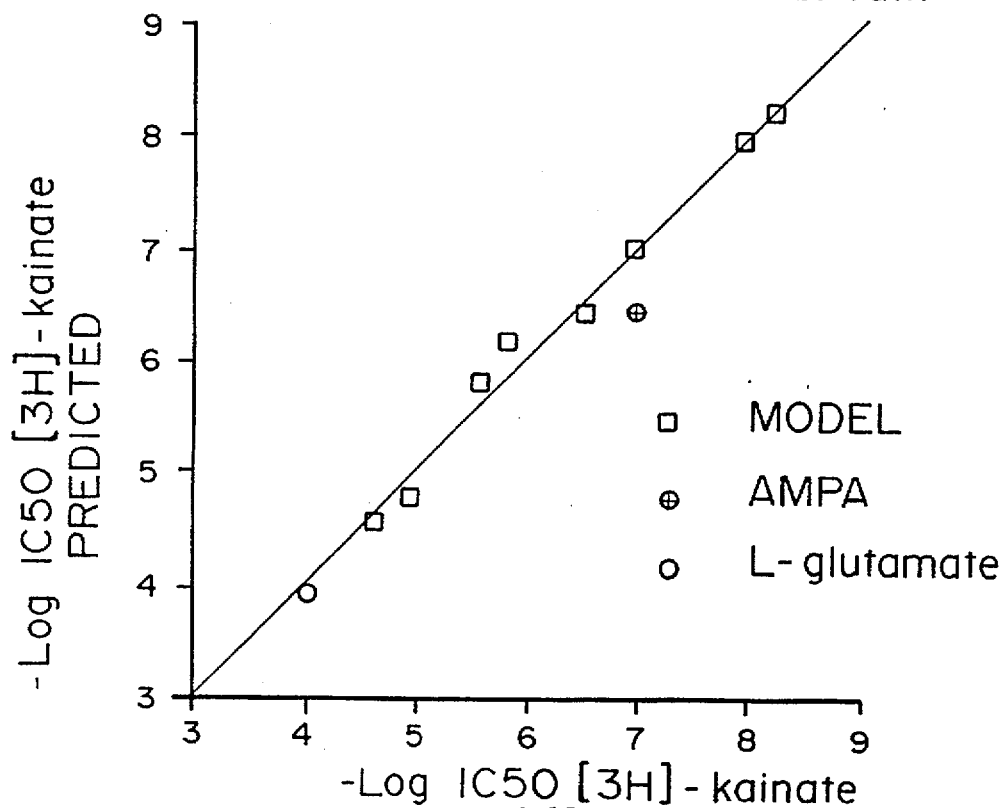
FIG. 4 is a graph of the Log $IC_{50}$ predicted [$^3$H]-kainate versus Log $IC_{50}$ actual [$^3$H]-kainate, for KA agonist model (squares), AMPA (circle with cross), and L-glutamate (circles).

Two known KA receptor agonists, L-glutamic acid and S-AMPA, were evaluated to test the utility of the receptor model and the QSAR equation. The model predicted the correct $IC_{50}$ values. FIG. 4 is a graph of the Log $IC_{50}$ predicted [$^3$H] kainate versus Log $IC_{50}$ actual [$^3$H] kainate, for the KA agonist model, AMPA, and L-glutamate.

The same methodologies can be applied to the AMPA receptor and other glutamate receptors.

IV. Pharmaceutical Compositions and Therapeutic Applications based on In vitro and In vivo studies Receptor Binding The basic discovery described herein is of a class of compounds that selectively bind at the KA receptor and modulate KA receptor function. Binding can be determined using standard techniques, to yield data such as that in Table 3. Modulation of the KA EAA receptor, as demonstrated by compounds showing potent in vitro affinity for the KA receptor, make the compounds useful for treating human neuropsychopharmacological conditions related to EAAs. Since the compounds described herein regulate the in vitro effects of KA, they are useful in the in vivo treatment of EAA dependent psychosis, neurodegeneration, convulsions, pain and learning and memory deficits.

The following analytical methods were used to determine the binding for each ligand and are identified by the literature reference where each is more fully set forth:

N-methyl-D-aspartate (NMDA) Receptor Binding Assay with CGS 19755:

Murphy, et al. "Binding of [$^3$H]-3-(2-carboxypiperazin-4-yl-D-propyl-1-phosphonic acid) to rat brain membranes: A selective, high affinity ligand of N-methyl-D-aspartate receptors" *J. Pharm. Exper. Therapeutics.* 240:778–784 (1987).

AMPA Receptor Binding Assay:

Murphy, et al. "Characterization of quisqualate recognition sites in rat brain tissue using [$^3$H]alpha-amino-3-hydroxy-5-methylisoxazole-4-propionic acid and a filtration assay" *Neurochemical Research.* 12:775–781 (1987).

KA Receptor Binding Assay with KA:

London, et al. "Specific binding of [$^3$H]kainic acid to receptor sites in rat brain". *Molecular Pharmacology.* 15:492-5-5 (1979).

The $IC_{50}$ values in Table 3 were determined according to these procedures by exposing the receptor preparation to a radiolabeled ligand and increasing amounts of test ligand. The amount of radioactivity bound to the receptor preparation will decrease in the presence of test compounds which compete for the binding site for the radiolabeled ligand.

TABLE 3

Binding of Compounds to Glutamate Receptor Preparations.

| Compound | R | NMDA [$^3$H]MK-801 EC$_{50}$ (µM) | NMDA CGS-19755 IC$_{50}$ (µM) | AMPA IC$_{50}$ (µM) | KA IC$_{50}$ (µM) |
|---|---|---|---|---|---|
| AMPA | NA | 5.6 | — | 0.005 | 2.g1 |
| kainic acid | NA | 34.6 | >100 | 5.1 | 0.011 |
| L-glutamate | H | 0.24 | 0.2 | 0.26 | 0.20 |
| 1 | CH$_3$ | 26.6 | 10 | >100 | 3.0 |
| 2 | CH$_3$ | 12.9 | 10 | 13.5 | 3.0 |
| 8 | CH$_3$ | 36.4 | 7 | >100 | 0.035 |
| 7 | CH$_3$ | 130 | 75 | 10 | 1.34 |

It can be seen from the data in Table 3 that the compounds described herein specifically bind to the Kainate receptor.

Since native KA receptors are heterogeneous, the properties of Example 5 were also examined in recombinant GluR6 receptors. These receptors exhibit saturable [$^3$H] kainate binding and produce rapidly desensitizing currents in response to KA and glutamate characteristic of native KA receptors. The K$_d$ of [$^3$H]kainate at GluR6 has previously been reported between 12.9 and 95 nM, and the K$_d$ obtained in this study is consistent with the former values. Differences in apparent affinity of [$^3$H]kainate may be attributable to both the expression systems and assay methods employed. The potency of Example 5 to inhibit [$^3$H]kainate binding to GluR6 was comparable to KA, and the increase in K$_d$ of [$^3$H]kainate (without a change in B$_{max}$) observed in the presence of Example 5 is consistent with a competitive mode of action. Based on the rank order of potencies of KA, domoate and NS-102, it has been concluded that GluR6 most closely resembles the "low" affinity form of KA receptors. In view of the apparent heterogeneity of wild type KA receptors, the observation that the apparent affinity of Example 5 was essentially equal to that of KA at GluR6 but 2–3 fold lower at both the "high" and "low" affinity forms of native KA receptors in rat brain indicates Example 5 may exhibit selectivity for some receptor subtypes.

In Vitro Assays of Physiological Activity and Potency

In combination, in vitro and in vivo assays are predictive of the activity of these compounds for treatment of patients. This is supported, for example, by U.S. Pat. No. 5,061,721 to Cordi et al. on the use of a combination of D-cycloserine and D-alanine to treat Alzheimer's disease, age-associated memory impairment, learning deficits, and psychotic disorders, as well as to improve memory or learning in healthy individuals, and U.S. Pat. No. 5,086,072 to Trullas et al. on 1-aminocyclo-propane carboxylic acid (ACPC), which modulates the NMDA receptor. As is now being tested in clinical trials, ACPC and its derivatives can be used to treat neuropharmacological disorders resulting from excessive activation of the NMDA receptor, such as occurs in ischemia. NMDA antagonists and partial agonists have clearly been shown to be useful in human clinical trials based on in vitro and in vivo assays, as described by Hutchinson, et al., *J. Med. Chem.* 32, 2171–2178 (1989). Hutchinson, et al., (1989) reported that 4-(phosphonomethyl)-2-piperidine carboxylic acid (CGS-19755), a competitive glutamate antagonist for the NMDA receptor, is active in animal models of neurodegenerative diseases such as stroke and is currently undergoing human clinical evaluation for the treatment of strokes and head trauma.

The following tests are used to demonstrate that binding activity correlates with physiological activity, both in vitro and in vivo. The results of these tests indicate that kainate antagonists and partial agonists will be effective clinically for treatment of a variety of disorders, including includes cognitive, learning, and memory deficits, chemical toxicity (including substance tolerance and addiction), excitotoxicity, neurodegenerative disorder (such as Huntington's disease, Parkinson's disease, and Alzheimer's disease), post-stroke sequelae, epilepsy, seizures, mood disorders (such as bipolar disorder, dysthymia, and seasonal affective disorder), depression, and pain. Neurodegenerative disorders can result from dysfunction or malfunction of the receptor.

Electrophysiology

Tissue slice or whole cell electrophysiology as described by Yamada (*Neurophysiology,* 1994 and references therein) is used to measure agonist, partial agonist, or antagonist properties of drugs for glutamate receptors. This is a useful assay to demonstrate the in vivo activity of compounds such as those described herein, since it is predictive of efficacy, defined as the potency of the compound. This is distinct from the binding affinity.

For example, whole cell electrophysiology shows that the compound of Example 8, (2S,4R)-4-methyl glutamic acid, modulates the KA but not the AMPA receptor. Rat GluR6 KA receptors were expressed in HEK 293 cells in culture and evaluated by the patch clamp technique. (2S,4R)-4-Methyl glutamic acid at doses of 10 nM to 20 µM completely and reversibly blocked the current evoked by 300 mM KA. (2S,4R)-4-Methyl glutamic acid can be administered in combination with a KA block several times without damage to the cells. In contrast, when rat GluR4 (AMPA) receptors were expressed in HEK 293 cells, concentrations of (2S,4R)-4-methyl glutamic acid up to 200 µM had no effect on currents evoked by 300 µM AMPA.

The same type of experiment was repeated with rat dorsal root ganglia in culture which express a high level of GluR5 KA receptors. 20 to 40 µM of (2S,4R)-4-methyl glutamic acid completely and reversibly blocked 300 µM KA induced currents. When the (2S,4R)-4-methyl glutamic acid was tested against the GluR4 AMPA receptor expressed in HEK 293 cells, doses up to 200 µM did not inhibit 300 µM AMPA currents, which demonstrate its selective modulation of KA versus AMPA receptors.

It is expected that the other compounds described herein will also selectively modulate the KA receptor.

The following assays can also be used to evaluate the physiological activity and potency of the compounds described herein.

Mongolian gerbil Forebrain Ischemia Assay

This assay is used to determine the extent of protection afforded by a test compound on neural brain cells subjected to ischemic conditions as a model of neurodegeneration. Male Mongolian gerbils are injected with the test compound prior to carotid occlusion. Flow is occluded for 4 to 5 min. and then opened and inspected to confirm reflow. Following surgery, the gerbils are kept alive for 7 days. They are anesthetized with pentobarbital and perfused transcardially with saline with heparin followed by buffered formalin. The brain is removed, trimmed, and prepared for histological processing. Sections are stained and damaged neurons in the CA1 region of the hippocampus are examined. The effects of the test compound are compared to untreated controls.

Based on the in vitro results described above, it is expected that cell loss will be significantly reduced in gerbils treated with the compounds described herein.

Rat Mechano-allodynia Pain Model:

This test is to determine the extent of protection by a test compound to neuropathic pain sensations. The model is described by Bennett, *Neuro. Report* 5, 1438–1440 (1994), and references cited therein. A rat is prepared by bilaterally exposing the sciatic nerves on both thighs. On one side, loosely fitting constrictive ligatures are tied around the nerve; the other side is sham manipulated but ligated. With the rat standing on an elevated perforated floor, mechano-allodynia is measured by applying from beneath a graded series of yon Frey hairs to the mid-plantar region of the effected paws. The hair that evokes at least one withdrawal response is designated the threshold level when compared to the sham treated nerve.

Mouse antidepressant Forced Swim Test

This test is to determine the extent of antidepressant activity of a test compound. The model described by Trullas, et al., *Eur. J. Pharm.* 185, 1–10 (1990), and the references cited therein. Mice are placed individually in a cylinder filled with water at 22°–25° C. The duration of immobility is scored during the last four minutes of a six minute test.

Cocaine-induced hypermotility

Kainate administered locally or cocaine administered subcutaneous (s.c.) induces an increase in dopamine release in nucleus accumbens and nucleus caudatus accompanied by stereotype behavior such as hyper-locomotion, rearing, sniffing, and grooming. These effects can be inhibited by KA receptor antagonists administered locally or systemically. Based on these observations, it has been concluded that non-NMDA receptors regulate the release of dopamine in the nucleus caudatus and that non-NMDA receptors antagonists can alleviate the symptoms of psychosis.

The compounds described herein should thereof eliminate or inhibit kainic acid or cocaine induced behavior.

Dosage Forms

Effective Dosage Ranges

The compounds described herein can be administered parenterally, either subcutaneously, intramuscularly, or intravenously, or alternatively, administered orally in a dose range of between approximately 0.1 mg/kg body weight and 150 mg/kg body weight.

Carriers and Additives

The active ingredient can be administered parenterally, in sterile liquid dosage forms. In general, water, a suitable oil, saline, aqueous dextrose, and related sugar solutions and glycols such as propylene glycol or polyethylene glycols are suitable carriers for parenteral solutions. Solutions for parenteral administration preferably contain a water soluble form of the active ingredient, suitable stabilizing agents, and, if necessary, buffer substances.

Antioxidizing agents such as sodium bisulfite, sodium sulfite, or ascorbic acid, either alone or in combination, can be used as suitable stabilizing agents. Also used are citric acid and its salts and sodium EDTA. In addition, parenteral solutions can contain preservatives, such as benzalkonium chloride, methyl- or propylparaben, and chlorobutanol.

The active ingredient can be administered orally in solid dosage forms, such as capsules, tablets and powders, or in liquid dosage forms, such as elixirs, syrups, and suspensions. Gelatin capsules contain the active ingredient and powdered carriers, such as lactose, starch, cellulose derivatives, magnesium stearate, or stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere.

Other agents that can be used for delivery include liposomes, microparticles (including microspheres and microcapsules), and other release devices and forms that provide controlled, prolonged or pulsed, delivery or which enhance passage through the blood brain barrier, for example.

Bioerodible microspheres can be prepared using any of the methods developed for making microspheres for drug delivery, for example, as described by Mathiowitz and Langer, *J. Controlled Release* 5,13–22 (1987); Mathiowitz, et al., *Reactive Polymers* 6, 275–283 (1987); and Mathiowitz, et al., *J. Appl. Polymer Sci.* 35, 755–774 (1988), the teachings of which are incorporated herein. The selection of the method depends on the polymer selection, the size, external morphology, and crystallinity that is desired, as described, for example, by Mathiowitz, et al., *Scanning Microscopy* 4,329–340 (1990); Mathiowitz, et al., *J. Appl. Polymer Sci.* 45, 125–134 (1992); and Benita, et al., *J. Pharm. Sci.* 73, 1721–1724 (1984), the teachings of which are incorporated herein. Methods routinely used by those skilled in the art include solvent evaporation, hot melt encapsulation, solvent removal, spray drying, phase separation and ionic crosslinking of gel-type polymers such as alginate or polyphosphazines or other dicarboxylic polymers to form hydrogels.

Other delivery systems including films, coatings, pellets, slabs, and devices can be fabricated using solvent or melt casting, and extrusion, as well as standard methods for making composites.

The microparticles can be suspended in any appropriate pharmaceutical carrier, such as saline, for administration to a patient. In the most preferred embodiment, the microparticles will be stored in dry or lyophilized form until immediately before administration. They will then be suspended in sufficient solution for administration. The polymeric microparticles can be administered by injection, infusion, implantation, orally, or administration to a mucosal surface, for example, the nasal-pharyngeal region and/or lungs using an aerosol, or in a cream, ointment, spray, or other topical carrier, for example, to rectal or vaginal areas. The other devices are preferably administered by implantation in the area where release is desired. The materials can also be incorporated into an appropriate vehicle for transdermal delivery as well as stents. Appropriate vehicles include ointments, lotions, patches, and other standard delivery means.

The references cited herein are specifically incorporated by reference.

Modifications and variations of the present invention will be obvious to those skilled in the art from the foregoing detailed description. Such modifications and variations are intended to come within the scope of the appended claims.

We claim:

1. A method for treating a disorder associated with excessive or insufficient activation of the KA subtype of the ionotropic EAA receptors in a patient in need thereof comprising administering to the patient an effective amount to alleviate the symptoms of the disorder of a pharmaceutical composition comprising a compound selectively modulating ion flow through the Kainate ("KA") receptor in combination with a pharmaceutically acceptable carrier for administration to a patient in need thereof, wherein the compound is an alkyl carboxy amino acid compound having the following formula:

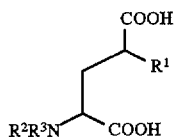

wherein:

$R^1$ is $CH_3$ or halogen;

$R^2$ and $R^3$ are independently selected from the group consisting of H, C1–C6-alkyl, C3–C4-alkenyl, C3–C5-cycloalkyl, C1–C6-alkyl-CO—, C1–C6-alkyl-OCO—, C1–C6-alkyl-NHCO—, —CHO, and C3–C6-alkynyl;

$R^2$ and $R^3$ taken together can be —$CH_2(CH_2)_pCH_2$—;

p is 0, 1, 2 or 3;

and pharmaceutically acceptable salts of these compounds.

2. The method of claim 1 wherein the disorder is selected from the group consisting of neurological, neuropsychological, neuropsychiatric, neurodegenerative, neuropsychopharmacological and functional disorders.

3. The method of claim 1 wherein the disorder is pain and the amount is effective to alleviate the pain.

4. The method of claim 1 wherein the disorder is selected from the group consisting of cognitive disorders associated with deactivation, suboptimal activation, and overactivation of the KA receptor.

5. The method of claim 1 wherein the disorder is a decrease of loss of memory, learning, or associated mental processes and the amount is effective to enhance or increase cognition.

6. The method of claim 1, wherein the compound is selected from the group consisting of:

(2S,4R)-4-methyl glutamic acid,
(2S,4S)-4-methyl glutamic acid,
(2R,4S)-4-methyl glutamic acid, and
(2R,4R)-4-methyl glutamic acid.

* * * * *